(12) United States Patent
Hama et al.

(10) Patent No.: US 8,252,565 B2
(45) Date of Patent: Aug. 28, 2012

(54) METHOD FOR PRODUCTION OF MICROBIAL FERMENTATION PRODUCT

(75) Inventors: Masakatsu Hama, Kamisu (JP);
Hiroyuki Konishi, Kamisu (JP);
Takaaki Watanabe, Ibaraki (JP);
Kazuhiro Onozuka, Kamisu (JP);
Shingo Koyama, Kamisu (JP)

(73) Assignee: Kao Corporation, Tokyo (JP)

( * ) Notice: Subject to any disclaimer, the term of this patent is extended or adjusted under 35 U.S.C. 154(b) by 483 days.

(21) Appl. No.: 12/529,716

(22) PCT Filed: Mar. 5, 2008

(86) PCT No.: PCT/JP2008/000456
§ 371 (c)(1),
(2), (4) Date: Sep. 3, 2009

(87) PCT Pub. No.: WO2008/108101
PCT Pub. Date: Sep. 12, 2008

(65) Prior Publication Data
US 2010/0028964 A1 Feb. 4, 2010

(30) Foreign Application Priority Data
Mar. 6, 2007 (JP) .................................. 2007-056104

(51) Int. Cl.
*C12P 7/02* (2006.01)
(52) U.S. Cl. ...................................................... 435/155
(58) Field of Classification Search ........................ None
See application file for complete search history.

(56) References Cited

U.S. PATENT DOCUMENTS

| | | | |
|---|---|---|---|
| 4,798,799 A | 1/1989 | Farbood et al. | |
| 4,970,163 A | 11/1990 | Farbood et al. | |
| 2005/0191629 A1 | 9/2005 | Walsem et al. | |

FOREIGN PATENT DOCUMENTS

| | | |
|---|---|---|
| EP | 0 204 009 A1 | 12/1986 |
| EP | 0 204 009 B1 | 12/1986 |
| JP | 62 74281 | 4/1987 |
| JP | 62-74281 | 4/1987 |
| JP | 3 224478 | 10/1991 |
| JP | 3-224478 | 10/1991 |
| JP | 4 136089 | 5/1992 |
| JP | 2005 534318 | 11/2005 |
| JP | 2007 252365 | 10/2007 |

OTHER PUBLICATIONS

Office Action issued Oct. 18, 2011 in Chinese Patent Application No. 200880007000.7 (with English translation).

*Primary Examiner* — Lisa J Hobbs
(74) *Attorney, Agent, or Firm* — Oblon, Spivak, McClelland, Maier & Neustadt, L.L.P.

(57) ABSTRACT

The present invention relates to a method for production of a diol form represented by the formula (2), which includes filtering a culture fluid obtained by microbial conversion using a compound represented by the following formula (1a) and/or formula (1b) as a substrate, using a filter having an aperture size of 10 to 100 μm; washing the residue on the filter with water or a solvent having an SP value outside the range of 8.3 to 20 $(cal/cm^3)^{1/2}$; subsequently dissolving the obtained cake in a solvent having an SP value of 8.3 to 20 $(cal/cm^3)^{1/2}$; and then filtering or centrifuging the solution.
According to the present invention, 1-(2-hydroxyethyl)-2,5,5,8a-tetramethyldecahydronaphthalen-2-ol, which is useful as an intermediate for the production of 3a,6,6,9a-tetramethyldodecahydronaphtho[2,1-b]furan, can be efficiently produced at high purity.

12 Claims, 1 Drawing Sheet

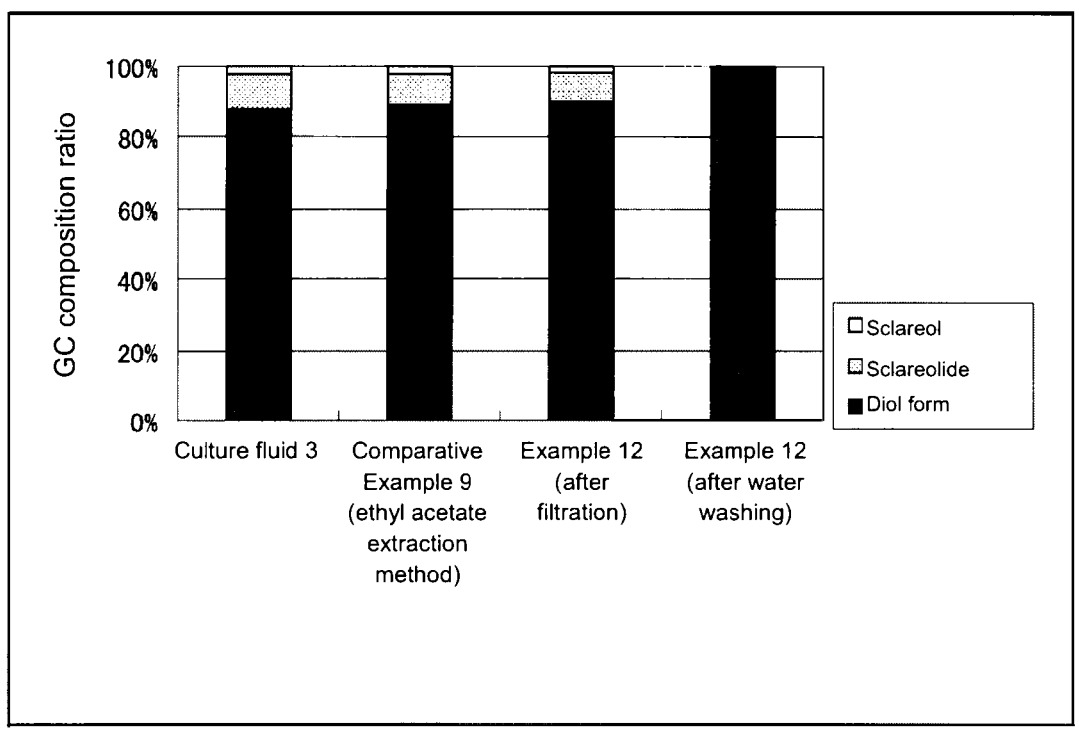

METHOD FOR PRODUCTION OF MICROBIAL FERMENTATION PRODUCT

FIELD OF THE INVENTION

The present invention relates to a method for production of a diol form that is useful as an intermediate for the production of 3a,6,6,9a-tetramethyldodecahydronaphtho[2,1-b]furan.

BACKGROUND OF THE INVENTION 3a,6,6,9a-tetramethyldodecahydronaphtho[2,1-b]furan (hereinafter, will be described as "compound A") is an aroma component contained in ambergris, which is a pathological secretion produced in the body of sperm whale, and is an important compound that is indispensable as an amber-based synthetic perfume. Compound A is produced mainly by a chemical synthesis method using sclareol, which is extracted from clary sage (*Salvia sclarea* L.), as a starting material. As the intermediates of compound A, 3a,6,6,9a-tetramethyl-decahydronaphtho[2,1-b]furan-2(1H)-one (hereinafter, indicated as "sclareolide") and 1-(2-hydroxyethyl)-2,5,5,8a-tetramethyldecahydronaphthalen-2-ol (hereinafter, indicated as "diol form") are known.

However, such a conventional method has a problem such that its environmental burden is heavy, and no sufficient yield or purity can be met. Meanwhile, methods for producing the compound A by obtaining an intermediate of the compound A from sclareol by microbial conversion and cyclizing this intermediate, have been reported (for example, Patent Documents 1 and 2).
[Patent Document 1] JP-A-03-224478
[Patent Document 2] JP-A-62-74281

DISCLOSURE OF THE INVENTION

The present invention provides a method for production of 1-(2-hydroxyethyl)-2,5,5,8a-tetramethyldecahydronaphthalen-2-ol represented by formula (2):

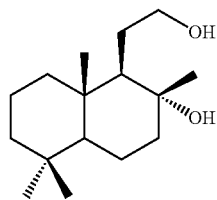

(2)

which includes filtering a culture fluid obtained by microbial conversion using a compound represented by the following formula (1a) and/or formula (1b) as a substrate:

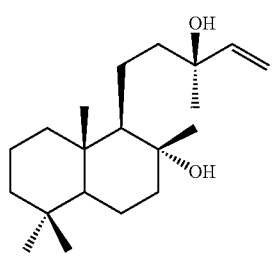

(1a)

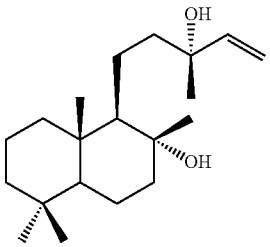

(1b)

through a filter having an aperture size of 10 to 100 µm; subsequently washing the residue on the filter with water or a solvent having an SP value outside the range of 8.3 to 20 $(cal/cm^3)^{1/2}$; subsequently dissolving the resulting cake with a solvent having an SP value of 8.3 to 20 $(cal/cm^3)^{1/2}$; and then filtering or centrifuging the solution.

BRIEF DESCRIPTION OF THE DRAWING

FIG. 1 is a diagram showing the compositions of the culture fluid 3, the fluid after filtration, the fluid after water washing (Example 12), and an extract obtained according to an ethyl acetate extraction method (Comparative Example 9).

DETAILED DESCRIPTION OF THE INVENTION

In regard to Patent Documents 1 and 2, separation and purification of the diol form obtained by microbial conversion is carried out by dissolving an extract which is obtained by solvent extracting a culture fluid with ethyl acetate and then drying, in warm hexane/ethyl acetate or hexane/chloroform, and crystallizing the diol form from the solution. However, the culture fluid contains unreacted sclareol or sclareolide, medium components and the like as a mixture, in addition to the diol form, therefore in the conventional solvent extraction methods using ethyl acetate and the like, components other than the diol form are also recovered at the same time. As such, separating and purifying the diol form alone turned out to be very difficult. Meanwhile, when the extract is washed with an acid or alkali solution by referring to the method for purification of sclareolide (U.S. Pat. No. 5,945,546), although a color improvement effect may be obtained, it turned out that no major change occurred in the composition, thereby making it impossible to obtain a high purity diol form.

Therefore, the present invention relates to a method for production of a diol form, by which a high-purity diol form can be produced efficiently.

The inventors of the present invention conducted researches on the means of separating and purifying a diol form, and as a result, found that while the diol form and sclareolide are both insoluble in water, these compounds can be separated by filtering the culture fluid through a filter having a specific mesh size and then washing with water. The inventors also found that the solubility of the diol form against specific solvents such as ethanol is high, and impurities can be removed by dissolving the cake obtained by water washing in these solvents, so that a high-purity diol form can be obtained in a high yield.

According to the present invention, a high-purity diol form, which is useful as an intermediate for the production of the compound A, can be produced efficiently.

In the present invention, the microorganism that can be used in the microbial conversion is not particularly limited as long as it is a microorganism having an ability to produce the diol form, which is an intermediate of the compound A, by using a compound represented by the formula (1a) and/or formula (1b) as a substrate, for example, microorganisms belonging to the class Ascomycetes, microorganisms belonging to the genus *Cryptococcus*, microorganisms belonging to the class Basidiomycetes, microorganisms belonging to the genus *Hyphozyma*, and the like may be mentioned. Among these, microorganisms belonging to the class Ascomycetes and microorganisms belonging to the genus *Hyphozyma* are preferred, from the viewpoint of the production efficiency for the diol form, which is an intermediate of the compound A. As for the microorganisms belonging to the class Ascomycetes, for example, there may be mentioned a microorganism designated as *Ascomycete* sp. KSM-JL2842 and deposited with the International Patent Organism Depositary at the National Institute of Advanced Industrial Science and Technology under the Accession No. FERM P-20759. As for the microorganisms belonging to the genus *Hyphozyma*, for example, the strain ATCC20624 described in Japanese Patent No. 2547713 may be mentioned.

The microorganism can be isolated from soil by evaluating an ability to produce the diol form, which is an intermediate of the compound A, as an indicator. The ability to produce the diol form, which is an intermediate of the compound A, can be evaluated by culturing a test microorganism in a culture medium containing the compound represented by the formula (1a) and/or formula (1b), and detecting the diol form, which is an intermediate of the compound A, contained in the medium. Detection of the diol form, which is an intermediate of the compound A, can be carried out using conventionally known analysis methods such as gas chromatography (GC), gas liquid chromatography (GLC), thin layer chromatography (TLC), high performance liquid chromatography (HPLC), infrared spectroscopy (IR), and nuclear magnetic resonance (NMR).

When the microorganism is cultured, the culture conditions are not particularly limited, and a medium of any composition can be used as long as the medium contains the compound represented by the formula (1a) and/or formula (1b) and enables the microorganism to grow therein. Examples of media that can be used include solid media and liquid media, which respectively contain carbon sources such as monosaccharides, disaccharides, oligosaccharides, polysaccharides, and organic acid salts; nitrogen sources such as inorganic and organic ammonium salts, nitrogen-containing organic substances, and amino acids; metallic minerals such as sodium chloride, ferrous sulfate, magnesium sulfate, manganese sulfate, zinc sulfate, and calcium carbonate; vitamins; and the like. Furthermore, a surfactant or an anti-foaming agent may also be added in accordance with the culture conditions.

Neither optimum pH range nor optimum temperature range is particularly limited. For example, an optimum pH range is pH 3 to 8, preferably pH 4 to 8, and more preferably pH 5 to 7, and an optimum temperature range is 10 to 35° C., preferably 15 to 30° C., and more preferably 20 to 30° C. The culture can be carried out utilizing shaking culture, anaerobic culture, static culture or culture using a fermentation bed, as well as resting cell reaction and immobilized cell reaction.

The concentration of the compound represented by the formula (1a) and/or formula (1b) that is added to the medium, is preferably 0.1 to 50% by mass, from the viewpoint of the production efficiency for the diol form which is an intermediate of the compound A. The substrate may be added to the medium prior to, or in the middle of, the culture.

According to the present invention, first, the culture fluid obtained by microbial conversion is filtered through a filter having an aperture size of 10 to 100 µm. Through this filtration, impurities such as the bacterial cells included in the culture fluid can be eliminated. If the aperture size of the filter is smaller than 10 µm, clogging and blocking may occur. On the other hand, if the aperture size is larger than 100 µm, the yield of the diol form becomes poor. The aperture size of the filter is preferably 10 to 90 µm, and more preferably 10 to 75 µm, from the viewpoint of enhancing the recovery ratio and purity of the diol form, and the aperture size is even more preferably 20 to 40 µm, from the viewpoints of recovery ratio, purity and filtration efficiency.

As for the filtering technique, any of suction filtration, pressure filtration and centrifugal filtration can be carried out, but from the viewpoint of yield, suction filtration is preferred. As for the material of the filter, various materials can be used, and specifically, filters made of resins such as polypropylene, polyester or nylon; filters made of ceramics; filters made of metals, and the like can be used. The liquid temperature at the time of filtration is preferably 0 to 80° C., more preferably 5 to 60° C., and even more preferably 10 to 35° C., from the viewpoints of recovery ratio, purity and filtration efficiency.

Subsequently, the residue on the filter is washed with water or a solvent having an SP value outside the range of 8.3 to 20 $(cal/cm^3)^{1/2}$. Through this washing operation, sclareol, sclareolide and impurities contained in the culture fluid, such as medium components, can be eliminated. If a solvent having an SP value within the range of 8.3 to 20 $(cal/cm^3)^{1/2}$ is used as the washing liquid, the solvent dissolves not only sclareol or sclareolide, but also the diol form. The solubility of the diol form in the solvent used herein is preferably 0.2% or less, and more preferably 0.1% or less. Here, the SP value represents the solubility parameter, and is described in, for example, reference literature "Fundamentals and Applications of SP Values and Calculation Methods" (Johokiko Co., Ltd., 2005), and the like. Examples of the solvent having an SP value outside the range of 8.3 to 20 $(cal/cm^3)^{1/2}$ include hexane (SP value 7.2), cyclohexane (SP value 8.2), water (SP value 23.4), a 30% or less aqueous solution of ethanol, and the like. These may be used individually or in combination of two or more species. A mixed solvent prepared by appropriately mixing solvents such as water, ethanol, methanol, acetone and ethyl acetate, and adjusting the SP value to fall outside the range of 8.3 to 20 $(cal/cm^3)^{1/2}$, may also be used. Furthermore, the SP value is a value at 20° C., and in the case of a mixed solvent, it is an SP value obtained after mixing. Here, as for the SP value of the mixed solvent, a value obtained by averaging the respective SP values of the solvents based on the volume ratio, is used. The washing liquid is preferably water or a solvent having an SP value outside the range of 8.3 to 20 $(cal/cm^3)^{1/2}$, and more preferably water or a solvent having an SP value outside the range of 7.5 to 20 $(cal/cm^3)^{1/2}$, from the viewpoint of enhancing the recovery ratio and purity of the diol form, and water is even more preferred. The liquid temperature of the washing liquid is preferably 0 to 80° C., more preferably 5 to 60° C., and even more preferably 10 to 35° C., from the viewpoints of recovery ratio, purity and filtration efficiency.

The frequency of the washing operation is preferably 1 to 6 times, and more preferably 2 to 3 times, from the viewpoint of eliminating sclareol or sclareolide, while allowing the diol form to remain behind. The amount of the washing liquid used in one operation of washing is preferably set to 100 mL per 100 mL of the culture fluid. The temperature of the washing liquid is preferably 5 to 90° C.

Subsequently, the cake obtained by separation and fractionation is dissolved in a solvent having an SP value of 8.3 to 20 $(cal/cm^3)^{1/2}$. A solvent having an SP value outside the range of 8.3 to 20 $(cal/cm^3)^{1/2}$ has low solubility for the diol form, and gives a poor yield.

Examples of the solvent having an SP value of 8.3 to 20 $(cal/cm^3)^{1/2}$ include lower alcohols such as methanol (SP value 14.5), ethanol (SP value 13.0), 1-propanol (SP value 12.0), 2-propanol (SP value 11.5), and 1-pentanol (SP value 10.6); ethyl acetate (SP value 9.1), acetic acid (SP value 10.5), ethylene glycol (SP value 16.1), diethylene glycol (SP value 14.6), glycerin (SP value 16.5), toluene (SP value 8.9), acetone (SP value 9.9), and the like. These may be used individually, or in combination of two or more species. A mixed solvent prepared by appropriately mixing solvents such as water, ethanol, methanol, acetone and ethyl acetate, and adjusting the SP value to fall in the range of 8.3 to 20 $(cal/cm^3)^{1/2}$, may also be used. Among these, from the viewpoint of enhancing the recovery ratio and purity of the diol form, a solvent having an SP value of 8.9 to 18.1 $(cal/cm^3)^{1/2}$ is preferred, a solvent having an SP value of 10.5 to 17 $(cal/cm^3)^{1/2}$ is more preferred, and ethanol or an aqueous solution of ethanol is even more preferred. The concentration of ethanol in the aqueous solution of ethanol is preferably a concentration of 60 to 99.5%, in view of the solubility of the diol form.

The amount of the solvent used in the dissolution of the cake is preferably 100 to 500 mL relative to 100 g of the cake, in view of the solubility of the diol form. The temperature of the solvent is preferably 20 to 60° C.

Subsequently, the solution is filtered or centrifuged to eliminate impurities such as the microorganism debris.

The size of the filter is preferably an aperture size of 0.1 to 10 µm, and more preferably an aperture size of 0.2 to 1 µm, from the viewpoint of enhancing the recovery ratio and purity of the diol form. As for the filtering technique and the material of filter, the same techniques and materials as described above may be mentioned.

The centrifuge is preferably a common apparatus, such as a separation plate type centrifuge, a cylinder type centrifuge or a decanter type centrifuge. The centrifugal conditions are such that the temperature is preferably 5 to 60° C., and more preferably 20 to 30° C., and the speed of rotation and the time are, for example, in the case of the cylinder type, preferably 2000 to 12000 r/min, more preferably 3000 to 12000 r/min, and even more preferably 10000 to 12000 r/min, for preferably 1 to 30 minutes, more preferably 2 to 10 minutes, and even more preferably 5 to 10 minutes.

A high purity diol form can be obtained from the resulting filtrate or supernatant with a good yield, by drying. The drying temperature is preferably from room temperature to 90° C., and drying under reduced pressure may also be performed.

The diol form is converted to the compound A by dehydrocyclization in various solvents, using an acidic catalyst, for example, p-toluenesulfonic acid, p-toluenesulfonic acid chloride, a catalytic amount of sulfuric acid and an acidic ion exchanger.

EXAMPLES

Microbial Conversion 1

One platinum loop of *Hyphozyma roseoniger* strain ATCC20624 was inoculated into 2.1% YM broth, and the system was subjected to shaking culture at 25° C. for three days. The resultant was used as an inoculum. Subsequently, the inoculum was inoculated into a medium containing 2.1% YM broth and 0.1% magnesium sulfate, and aerated stirred culture was carried out in a 1-L fermenter at 25° C., 0.5 vvm and 400 r/min for two days. Then, a substrate formed from 10% Tween 80 and 20% sclareol was added at an appropriate time such that the final concentration reached 4% of sclareol, and for 5 days from the addition of substrate, aerated stirred culture was performed while controlling the pH condition to pH 6.0 using 1N NaOH and 1N HCl. The resulting culture fluid was designated as culture fluid 1.

Microbial Conversion 2

One platinum loop of the strain *Ascomycete* sp. KSM-JL2842 was inoculated into 2.1% YM broth, and the system was subjected to shaking culture at 25° C. for three days. The resultant was collected and washed three times with physiological saline, and then was mixed with a medium formed from a 0.1 M phosphate buffer solution (pH 6.0), 0.1% magnesium sulfate, 3% Tween 80 and 6% sclareol. The mixture was subjected to a resting cell reaction in a 1-L fermenter at 25° C., 0.5 vvm and 400 r/min for 10 days.

The resulting culture fluid was designated as culture fluid 2.

Microbial Conversion 3

Culture was carried out by the same method as that used in the microbial conversion 1, except that the bacterial strain used was the strain *Ascomycete* sp. KSM-JL2842. The resulting culture fluid was designated as culture fluid 3.

Analysis Method

In regard to the analysis method for sclareol, sclareolide and diol form, the compounds were extracted with ethyl acetate and appropriately diluted, and a gas chromatography (GC) analysis was performed. The GC analysis was performed with a 6890N GC System (Agilent Technologies, Inc.), and the analysis conditions were as follows. An FID (Flame Ionization Detector) (Agilent Technologies, Inc.) was used as a detector, the injection inlet temperature was 250° C., and the injection method was carried out in the split mode (split ratio 100:1). The total flow was 200 ml/min, the column flow rate was 0.4 ml/min, the column used was DB-WAX (φ0.1 mm×10 m) (J&W Technology, Ltd.), and the oven temperature was 250° C.

Examples 1 to 4

The culture fluid 1 (30 mL) obtained by microbial conversion using the strain ATCC20624, was subjected to suction filtration with filters having an aperture size indicated in Table 1, respectively. Subsequently, washing was repeated three times using 30 mL of distilled water (SP value 23.4). The temperature at the time of filtration and washing was room temperature (20° C.). Subsequently, the resulting cakes were dissolved in ethanol (Wako Pure Chemical Industries, Ltd., special grade reagent) (SP value 13.0) (30 mL) respectively, and each solution was filtered with a 0.2-µm filter. Then, the filtrates were dried under reduced pressure, to obtain crystals of the diol form, respectively. The results are presented in Table 1.

Comparative Examples 1 and 2

Crystals of the diol form were obtained in the same manner as in Example 1, except that the culture fluid 1 obtained by microbial conversion using the strain ATCC20624 was subjected to suction filtration with filters having an aperture size of 5 µm and 150 µm, respectively. The results are presented in Table 1.

Comparative Example 3

The culture fluid 1 (20 mL) obtained by microbial conversion using the strain ATCC20624 was mixed with ethyl acetate (Wako Pure Chemical Industries, Ltd., special grade reagent) (60 mL), the mixture was centrifuged (3000 rpm, for 5 minutes), and then the supernatant (54 mL) was recovered. Subsequently, the supernatant was further centrifuged (3000 rpm, for 5 minutes), and then the supernatant was recovered and dried under reduced pressure, to thereby obtain crystals of the diol form. The results are presented in Table 1.

Comparative Example 4

The culture fluid 1 (20 mL) obtained by microbial conversion using the strain ATCC20624 was centrifuged (3000 rpm, for 5 minutes), and then the precipitate was recovered and mixed with ethyl acetate (Wako Pure Chemical Industries, Ltd., special grade reagent) (60 mL). Subsequently, this mixture liquid was further centrifuged (3000 rpm, for 5 minutes), and then the supernatant was recovered and dried under reduced pressure, to thereby obtain crystals of the diol form. The results are presented in Table 1.

TABLE 1

|  | Filter aperture size (μm) | Purity of diol form (%) | Yield of diol form (%) |
| --- | --- | --- | --- |
| Example 1 | 10 | 78.4 | 96.2 |
| Example 2 | 40-50 | 76.6 | 95.2 |
| Example 3 | 75 | 79.3 | 96.0 |
| Example 4 | 100 | 78.9 | 94.9 |
| Comparative Example 1 | 5 | Blocked | Blocked |
| Comparative Example 2 | 150 | — | 22.3 |
| Comparative Example 3 | — | 72.7 | 95.1 |
| Comparative Example 4 | — | 74.6 | 89.5 |

From the results of the Table 1, it was found that a high purity diol form is obtained with a good yield by suction filtering the culture fluid using a filter having an aperture size of 10 to 100 μm, whereas the diol form cannot be recovered due to blockage when a filter having an aperture size of 5 μm is used, while the yield of the diol form becomes poor when a filter having an aperture size of 150 μm is used. It was also found that when the culture fluid is extracted directly with ethyl acetate, the diol form cannot be separated from sclareol or sclareolide in the culture fluid, and the diol form cannot be obtained at high purity. Furthermore, it was found that when the culture fluid is centrifuged, and then the supernatant is removed and extracted with ethyl acetate, not only the diol form cannot be obtained at high purity, but also the yield becomes poor.

Examples 5 to 9

The culture fluid 2 (30 mL) obtained by microbial conversion using the strain *Ascomycete* sp. KSM-JL2842, was subjected to suction filtration with filters having an aperture size as indicated in Table 2, respectively. Subsequently, washing was repeated three times using 30 mL of distilled water (SP value 23.4). The temperature at the time of filtration and washing was room temperature (20° C.). Subsequently, the resulting cakes were respectively dissolved in ethanol (Wako Pure Chemical Industries, Ltd., special grade reagent) (SP value 13.0) (30 mL), and the respective solutions were filtered with a 0.2-μm filter. Then, the filtrates were dried under reduced pressure, to obtain crystals of the diol form, respectively. The results are presented in Table 2.

Comparative Example 5

The culture fluid 2 (20 mL) obtained by microbial conversion using the strain *Ascomycete* sp. KSM-JL2842 was mixed with ethyl acetate (Wako Pure Chemical Industries, Ltd., special grade reagent) (60 mL), the mixture was centrifuged (3000 rpm, for 5 minutes), and then the supernatant (54 mL) was recovered. Subsequently, the supernatant was further centrifuged (3000 rpm, for 5 minutes), and then the supernatant was recovered and dried under reduced pressure, to thereby obtain crystals of the diol form. The results are presented in Table 2.

Comparative Example 6

The culture fluid 2 (20 mL) obtained by microbial conversion using the strain *Ascomycete* sp. KSM-JL2842 was centrifuged (3000 rpm, for 5 minutes), and then the precipitate was recovered and mixed with ethyl acetate (Wako Pure Chemical Industries, Ltd., special grade reagent) (60 mL). Subsequently, this mixture liquid was further centrifuged (3000 rpm, for 5 minutes), and then the supernatant was recovered and dried under reduced pressure, to thereby obtain crystals of the diol form. The results are presented in Table 2.

TABLE 2

|  | Filter aperture size (μm) | Purity of diol form (%) | Yield of diol form (%) |
| --- | --- | --- | --- |
| Example 5 | 10 | 95.5 | 95.1 |
| Example 6 | 20 | 96.2 | 93.2 |
| Example 7 | 40 | 95.9 | 93.4 |
| Example 8 | 75 | 96.6 | 91.9 |
| Example 9 | 100 | 96.2 | 92.5 |
| Comparative Example 5 | — | 92.2 | 90.9 |
| Comparative Example 6 | — | 93.5 | 79.3 |

From the results given above, it was found that when the culture fluid is filtered using a filter having an aperture size of 10 to 100 μm and washed with water, and then the resulting cake is dissolved in ethanol and then filtered through a filter, a high purity diol form is obtained with a good yield.

Example 10

The culture fluid 2 (30 mL) obtained by microbial conversion using the strain *Ascomycete* sp. KSM-JL2842, was subjected to suction filtration with a filter having an aperture size of 10 μm. Subsequently, washing was repeated three times using 30 mL of a 20% aqueous solution of ethanol (SP value 21.3). The temperature at the time of filtration and washing was room temperature (20° C.) Subsequently, the resulting cake was dissolved in ethanol (Wako Pure Chemical Industries, Ltd., special grade reagent) (SP value 13.0) (30 mL). This solution was filtered with a 0.2-μm filter, and then dried under reduced pressure, to thereby obtain crystals of the diol form. The results are presented in Table 3.

Example 11

Crystals of the diol form were obtained in the same manner as in Example 10, except that washing was repeated three times using 30 mL of a 30% ethanol solution (SP value 20.3), the resulting cake was dissolved in ethanol (Wako Pure Chemical Industries, Ltd., special grade reagent) (SP value 13.0) (30 mL), and then the solution was filtered with a 0.2-μm filter.

Comparative Examples 7 and 8

Crystals of the diol form were obtained in the same manner as in Example 10, except that the culture fluid was suction filtered with filters having an aperture size as indicated in Table 3, respectively, and was washed using 30 mL of a 40% aqueous solution of ethanol (SP value 19.3). The results are presented in Table 3.

TABLE 3

| | Filter aperture size (μm) | Ethanol concentration (%) (SP value) | Purity of diol form (%) | Yield of diol form (%) |
|---|---|---|---|---|
| Example 10 | 10 | 20 (21.3) | 97.0 | 90.6 |
| Example 11 | 10 | 30 (20.3) | 97.3 | 90.7 |
| Comparative Example 7 | 20 | 40 (19.3) | 96.7 | 73.2 |
| Comparative Example 8 | 40 | 40 (19.3) | 97.4 | 62.8 |

From the results of the Table 3, it was found that only the diol form can be separated and purified by washing with a solvent having an SP value outside the range of 8.3 to 20 $(\text{cal/cm}^3)^{1/2}$, whereas if washing is performed using a solvent having an SP value in the range of 8.3 to 20 $(\text{cal/cm}^3)^{1/2}$, the diol form also dissolves out together with sclareol and sclareolide, and a high purity diol form cannot be obtained with a good yield.

Example 12

The culture fluid 3 (200 mL) obtained by microbial conversion using *Ascomycete* sp. KSM-JL2842, was suction filtered through a 400-mesh (34 μm) filter, and then washing was repeated six times using 200 mL of distilled water (SP value 23.4). The temperature at the time of filtration and washing was room temperature (20° C.) The results are presented in Table 4 and FIG. 1.

Comparative Example 9

The culture fluid 3 (100 mL) obtained by microbial conversion using *Ascomycete* sp. KSM-JL2842, which is the same strain as that used in Example 12, was mixed with ethyl acetate (Wako Pure Chemical Industries, Ltd., special grade reagent) (150 mL), and the ethyl acetate layer (145 mL) was recovered. Subsequently, the ethyl acetate layer was filtered with a 0.2-μm filter, and the filtrate was recovered and dried under reduced pressure, to obtain crystals of the diol form. The temperature at the time of filtration was room temperature (20° C.). The results are presented in Table 4 and FIG. 1.

TABLE 4

| | Diol form (%) | Sclareolide (%) | Sclareol (%) |
|---|---|---|---|
| Culture fluid 3 | 87.9 | 10.1 | 2.0 |
| Example 12 (after filtration) | 89.9 | 8.7 | 1.4 |
| Example 12 (after water washing) | 99.2 | 0.3 | 0.5 |
| Comparative Example 9 (ethyl acetate extraction method) | 88.9 | 8.8 | 2.3 |

From the results of the Table 4, it was found that the purity of the diol form is increased when purification is performed according to the method of the present invention, as compared to the purification according to an ethyl acetate extraction method.

The invention claimed is:

1. A method for obtaining a purified diol compound 1-(2 hydroxyethyl)-2,5,5,8a-tetramethyldecahydronaphthalen-2-ol represented by the formula (2):

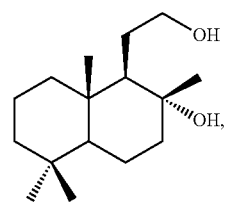

(2)

the method comprising:

culturing at least one microorganism, adding, prior to or during said culturing, at least one substrate compound represented by the following formula (1a) and/or formula (1b):

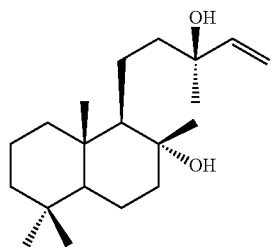

(1a)

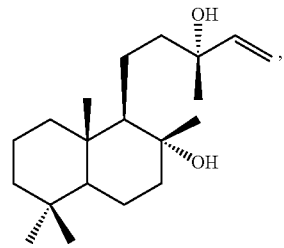

(1b)

obtaining a diol compound 1-(2-hydroxyethyl)-2,5,5,8a-tetramethyldecahydronaphthalen-2-ol of the formula (2) in a culture fluid of the cultured microorganism by microbial conversion of the substrate compound

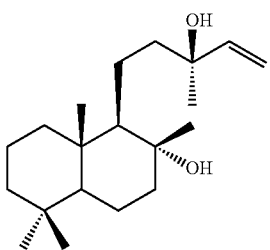
(1a)

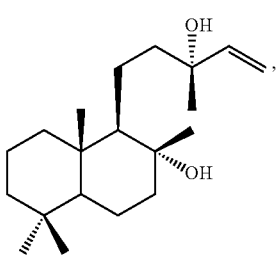
(1b)

filtering the culture fluid containing the diol compound with a filter having an aperture size of 10 to 100 μm;

washing a residue on the filter with water or a solvent having an SP value outside the range of 8.3 to 20 (cal/cm$^3$)$^{1/2}$, thereby obtaining a cake;

dissolving the obtained cake in a solvent having an SP value of 8.3 to 20 (cal/cm$^3$)$^{1/2}$, thereby obtaining a solution of the diol compound; and filtering or centrifuging the solution, thereby obtaining the purified diol compound.

2. The method according to claim 1, wherein the solvent having an SP value outside the range of 8.3 to 20 (cal/cm$^3$)$^{1/2}$ is at least one solvent selected from the group consisting of hexane, cyclohexane, a 30% or less aqueous solution of ethanol, and water, and the solvent having an SP value of 8.3 to 20 (cal/cm$^3$)$^{1/2}$ is at least one solvent selected from the group consisting of ethanol, methanol, 1-propanol, 2-propanol, acetic acid, toluene, ethyl acetate, 1-pentanol, acetone, and diethylene glycol.

3. The method according to claim 1 or 2, wherein the culture fluid comprises the substrate compound represented by the formula (1a), and/or the substrate compound represented by the formula (1b), 3a,6,6,9a-tetramethyldecahydronaphtho[2,1-b]furan-2(1H)-one, and 1-(2-hydroxyethyl)-2,5,5,8a-tetramethyldecahydronaphthalen-2-ol represented by the formula (2).

4. The method according to claim 1, wherein the microorganism belongs to the class Ascomycetes, the genus *Cryptococcus*, the class Basidiomycetes, and/or the genus *Hyphozyma*.

5. The method according to claim 1, wherein the microorganism is cultured in a solid or liquid medium.

6. The method according to claim 1, wherein a pH in culturing is from 3 to 8 and an optimum temperature is from 10 to 35° C.

7. The method according to claim 1, wherein a concentration of the substrate compound in a culture medium at the time of the addition of the at least one substrate compound is from 0.1 to 50% by mass, and the substrate compound is added to the culture medium prior to or during said culturing the microorganism.

8. The method according to claim 1, wherein said washing is conducted from 1 to 6 times.

9. The method according to claim 1, wherein the amount of the solvent in said dissolving the obtained cake is from 100 to 500 ml relative to 100 g of the cake and a temperature of the solvent is from 20 to 60° C.

10. The method according to claim 1, wherein after said dissolving the obtained cake, the filtering is conducted with a filter having an aperture size of from 0.1 to 10 μm.

11. The method according to claim 1, wherein after said dissolving the obtained cake, the centrifuging is conducted at a temperature of from 5 to 60° C. and a speed of rotation from 2,000 to 12,000 r/min for 1 to 30 minutes.

12. The method according to claim 1, further comprising drying the resulting filtrate at a temperature from room temperature to 90° C.

* * * * *

UNITED STATES PATENT AND TRADEMARK OFFICE
CERTIFICATE OF CORRECTION

PATENT NO. : 8,252,565 B2
APPLICATION NO. : 12/529716
DATED : August 28, 2012
INVENTOR(S) : Masakatsu Hama et al.

It is certified that error appears in the above-identified patent and that said Letters Patent is hereby corrected as shown below:

On the title page, Item (75),

"Inventors: Masakatsu Hama, Kamisu (JP);
Hiroyuki Konishi, Kamisu (JP);
Takaaki Watanabe, Ibaraki (JP);
Kazuhiro Onozuka, Kamisu (JP);
Shingo Koyama, Kamisu (JP)"

should read: --Inventors: Masakatsu Hama, Kamisu (JP);
Hiroyuki Konishi, Kamisu (JP);
Takaaki Watanabe, Kamisu (JP);
Kazuhiro Onozuka, Kamisu (JP);
Shingo Koyama, Kamisu (JP)--.

Signed and Sealed this
Thirteenth Day of November, 2012

David J. Kappos
*Director of the United States Patent and Trademark Office*